United States Patent [19]
Wiedner

[11] Patent Number: 5,345,616
[45] Date of Patent: Sep. 13, 1994

[54] PAIR OF GOGGLES WITH PAD ELEMENTS AT THE ENDS OF THE TEMPLES OR AT THE NOSE PIECE

[75] Inventor: Klaus Wiedner, Fürth/Bay, Fed. Rep. of Germany

[73] Assignee: Uvex Safety, LLC, Smithfield, R.I.

[21] Appl. No.: 96,057

[22] Filed: Jul. 22, 1993

Related U.S. Application Data

[63] Continuation of Ser. No. 910,642, Jul. 8, 1992, abandoned.

[30] Foreign Application Priority Data

Aug. 30, 1991 [DE] Fed. Rep. of Germany ....... 9110752
Feb. 15, 1992 [DE] Fed. Rep. of Germany ....... 9201984

[51] Int. Cl.$^5$ .................. A61F 9/02; G02C 5/12; G02C 5/16
[52] U.S. Cl. .................. 2/446; 2/448; 351/78; 351/87; 351/123; 351/136
[58] Field of Search .............. 2/446, 448; 351/78, 351/80, 82, 87, 123, 136, 138, 81, 137, 122

[56] References Cited

U.S. PATENT DOCUMENTS

| 260,928 | 7/1882 | Bausch | 351/123 |
|---|---|---|---|
| 1,145,786 | 7/1915 | Murray | 351/123 |
| 1,719,957 | 7/1929 | Arrick | 351/123 |
| 2,280,666 | 4/1942 | Schofield | 351/123 |
| 2,561,402 | 7/1951 | Nelson | 351/123 |
| 2,561,403 | 7/1951 | Nelson | 351/82 |
| 3,049,973 | 8/1962 | Moeller | 351/138 |
| 3,597,053 | 8/1971 | Masterman | 351/136 |
| 4,142,784 | 3/1979 | Bononi | 351/136 |

FOREIGN PATENT DOCUMENTS

| 137111 | 5/1950 | Australia | 351/87 |
|---|---|---|---|
| 116817 | 5/1990 | Japan | 351/123 |
| 656234 | 6/1986 | Switzerland . | |

*Primary Examiner*—Clifford D. Crowder
*Assistant Examiner*—Michael A. Neas
*Attorney, Agent, or Firm*—Salter & Michaelson

[57] ABSTRACT

For a pair of goggles with a frame and temples made of relatively hard plastic material or of metal comprising at least one pad element made of relatively soft plastic material at the ends of the temples and/or at the nose piece it is provided for the purpose of increasing the wearing comfort of the goggles and for attaining a stable fit, as is necessary in particular with protective goggles for workers and sports goggles, that the pad element is formed as a relatively thin-walled convexity which is moulded of plastic material.

15 Claims, 2 Drawing Sheets

PAIR OF GOGGLES WITH PAD ELEMENTS AT THE ENDS OF THE TEMPLES OR AT THE NOSE PIECE

This is a continuation of application Ser. No. 07/910,642 filed Jul. 8, 1993 now abandoned.

FIELD OF THE INVENTION

The invention relates to a pair of goggles comprising a frame and temples made of relatively hard plastic material or of metal with at least one pad element made of relatively soft plastic material at the ends of the temples and/or at the nose pieces of the frame.

BACKGROUND OF THE INVENTION

It is true that flames of goggles made of relatively hard plastic material or of metal show on the one hand a high stability and correspondingly enable elegant and simple designs, but on the other hand bruises may occur above all in the vicinity of the bridge of the nose and behind the ears, in particular if the person wearing the goggles moves its head often or while strongly changing direction, as it is the case when flames of goggles of this type are used with protective goggles for workers or with sports goggles.

In order to avoid these problems in this case, it is known to use pad elements made of softer plastic material or cushions made of softer plastic material with inclusion of fluid or air. Cushions of the generic type are for example known from CH 656 234 A5 in connection with protective goggles for workers.

Most of the cushion-like pad elements of this type are secured to the goggles by adhesion or by locking into recesses, i.e. these are elements manufactured separately, which have to be assembled thereafter and which can naturally be inadvertently released from the flames of the goggles.

Other known solutions provide e.g. injection moulding of the entire end of the temple with a softer plastic material, in order to avoid bruises. On the other hand this leads to the fact that the stability of the fit is impaired, what is in turn particularly disadvantageous with protective goggles for workers and sports goggles.

Finally it is also known to mould a softer plastic material onto the relevant places in the vicinity of the nose piece and of the ends of the temples in order to attain a padding effect. In fact by means of this the risk of pressure is slightly reduced, but a really good padding is not attained.

SUMMARY OF THE INVENTION

With the above considerations in mind it is the object of the invention to embody a pair of goggles of the aforementioned type with pad elements in such a manner, that a softness of the padding, which can be individually adapted to the respective purpose of application, is feasible in a simple manner with regard to manufacturing.

This object is attained according to the invention by the pad element being formed as a relatively thin-walled convexity which is moulded of plastic material.

A convexity of this type shows very good spring properties, which in addition can be easily adjusted by the appropriate selection of the hardness of the plastic material, the geometry of the convexity and also the thickness of the layer forming the convexity.

In a further embodiment of the invention it is provided that a pad element made of relatively soft plastic material is moulded in one piece on a supporting basic body of a nose piece or of the ear section of the temple made of relatively hard plastic material. The moulding of the basic body and of the soft plastic material can be done in one and the same mould.

Accordingly the spring effect is not only determined by the thin, bubbles-like configuration of the pad element, but also by the used plastic material, which is softer compared with the supporting basic material.

Advantageously the pad element which is convexed like bubbles embraces an approximately oval basic surface region, which is open in the region facing away from the side of contact.

Insofar according to the invention no closed air bubble is provided, but a bubble which is open on one side.

The pad element can comprise advantageously a reinforced free outer edge, by the dimensioning of which the stability of the element can be adjusted.

When putting the invention into practice in the nose region it can be provided that the nose piece is formed as a separate element, which can be placed onto the frame and/or the sight piece or the sight pieces, or as an alternative, that the nose piece is formed in one piece with the frame. In both cases it is possible to directly mould the pad element.

In the manufacture of pad elements in the nose region as well as at the end of the temple it is possible to attain the pad element by co-moulding with the plastic material of the basic material, which could be realized in particular in the vicinity of the end of the temple with excellent results.

Further details of the invention will become apparent from the ensuing description of preferred examples of embodiment of the invention taken in conjunction with the drawing.

DESCRIPTION OF THE PREFERRED EMBODIMENTS

Figure 1:
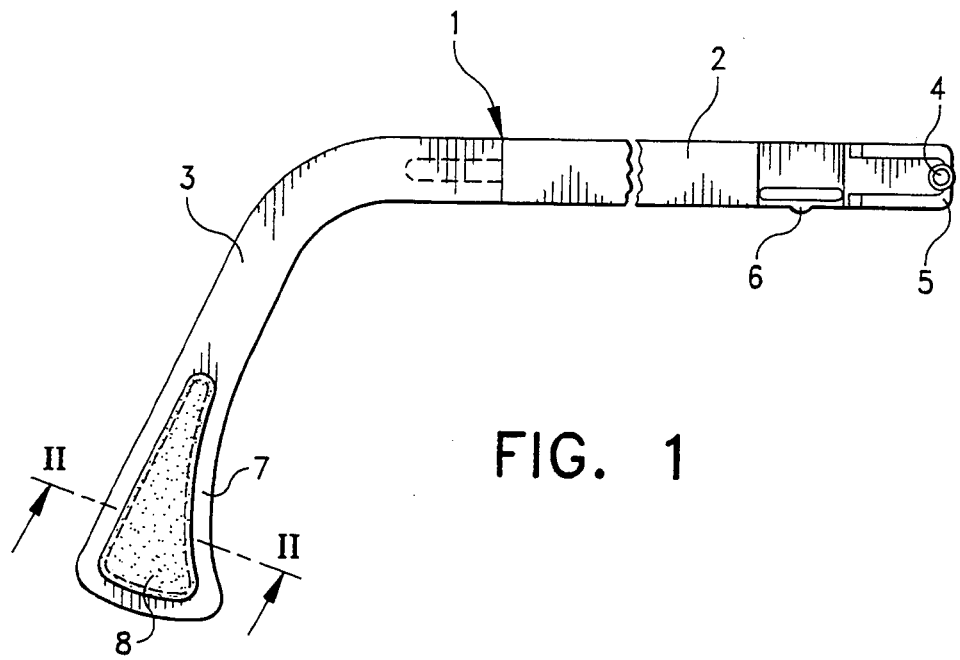
FIG. 1 shows a side view of a temple of the goggles formed according to the invention.
Figure 2:
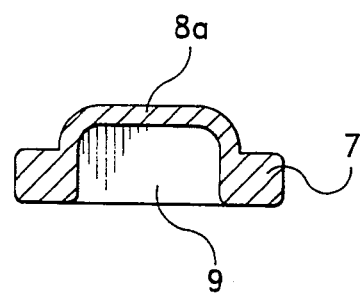
FIG. 2 shows a section taken along the line II—II in FIG. 1.
Figure 3:
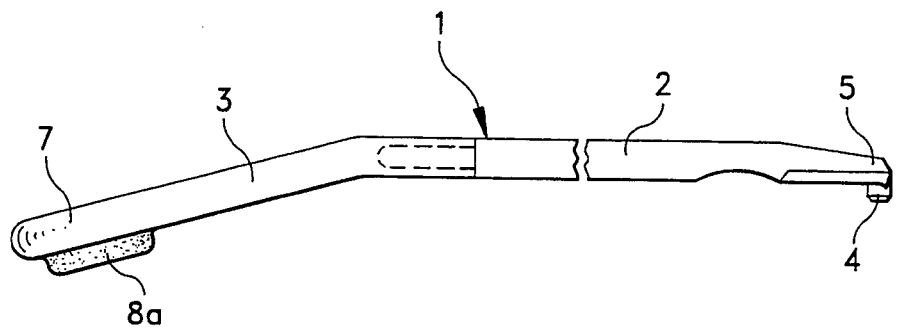
FIG. 3 shows a plan view onto the temple of the goggles in accordance with FIG. 1.

In FIG. 1 to 3 a temple 1 is illustrated for a pair of goggles, e.g. a pair of protective goggles for workers, which temple 1 comprises an essentially straight front hinge section 2 and an ear temple section 3, which is bent in relation to the hinge section 2.

The hinge section 2 comprises a hinge journal pin 4 at the free front end 5 and a locking projection 6 for performing length adjustment.

The ear temple section 3 has a widened end, at which a pad element 8 is formed.

As can be seen in particular from FIGS. 2 and 3, the pad element 8 is formed by the fact that the widened end 7 of the temple 1 has a convexity 8a, which is thin-walled like a membrane and which covers a recess 9 in the end 7 of the temple 1 and which is curved inwards in relation to the temple end 7 in such a manner that this convexity 8a is soft and elastic.

Figure 4:
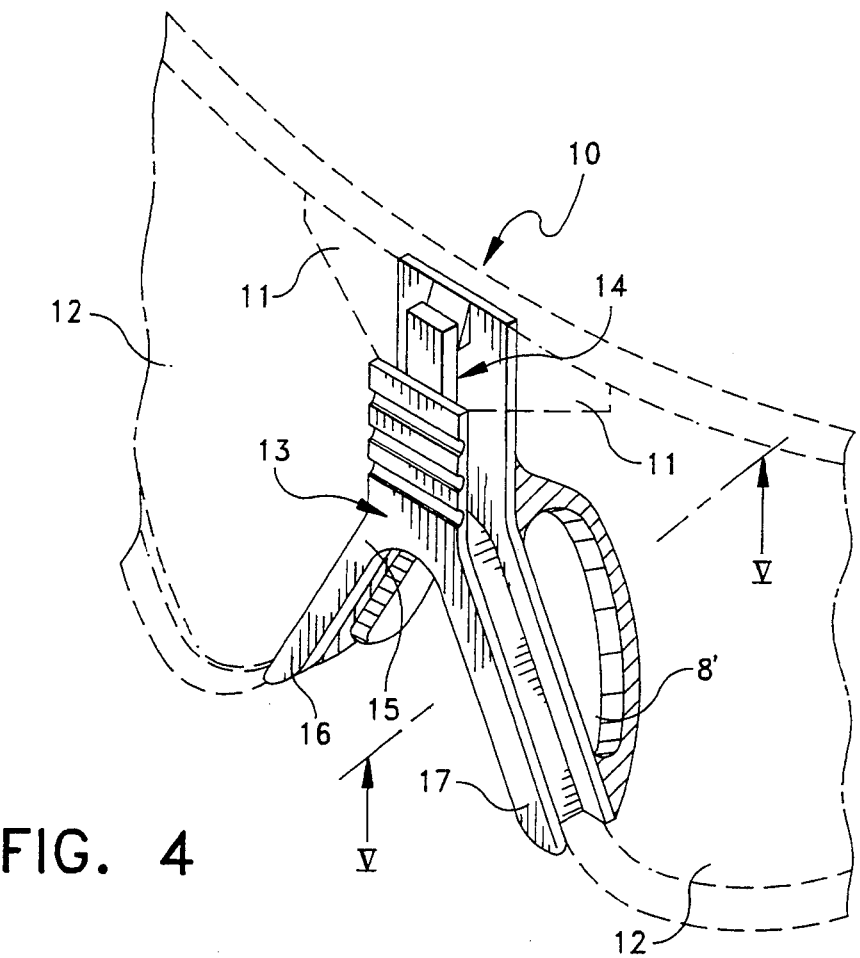
FIG. 4 shows a perspective view of the nose region of a pair of goggles according to the invention and FIG. 5 shows a section taken along the line IV—IV in FIG. 4.
Figure 5:
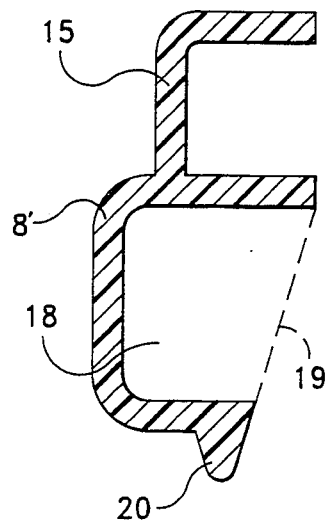

In FIG. 4 and 5 the realization of the pad element 8' in the nose piece region is illustrated. The pair of goggles 10 shown in FIG. 4 comprises holding elements 11 for the sight pieces 12, as shown in dashed lines. In the nose region a separate nose piece 13 is disposed, which is lockable into the above-disposed frame and holding element 11 via a locking arrangement 14.

The nose piece 13 comprises a supporting basic body 15, which is formed in the shape of a V at its underside, the V-legs 16, 17 being formed respectively by U-profiles which are open at the outside. At the rear side or inner side of each profile of this type a pad element 8' made of relatively soft plastic material is joined which is directly moulded by two-component injection moulding.

Each pad element 8' has a bubbles-like convexed configuration, whereby a hollow space 18 is formed, which is open away from the wearers nose. The free outer edge 20 of the pad element 8' formed in this manner is convex-like formed in reinforced manner.

What is claimed is:

1. A pair of goggles comprising a frame and a pair of temples having rear ends and extending from said frame, said temples each comprising a pad element adjacent the rear end thereof made form a relatively soft resilient plastic material, each pad element having a bubble-like convex inner side facing inwardly toward the head of the wearer for resiliently contacting the head of the wearer, each pad element also having a concave outer side facing outwardly away from the head of the wearer and defining an unobstructed hollow open area to permit outward flexing of each pad element in a direction away from the head of the wearer.

2. In the pair of goggles of claim 1, each of said temples comprising a basic body portion made from a relatively hard plastic material and one of said pad elements integrally molded in one piece therewith.

3. In the pair of goggles of claim 1, each of said pad elements including a reinforced outer edge.

4. In the pair of goggles of claim 2, each of said basic body portions being molded with the pad element thereof in an injection molding process.

5. In the pair of goggles of claim 1, each of said pad elements being of approximately oval configuration.

6. A pair of goggles comprising a pair of temples and a frame including a pair of opposed, inwardly facing nose pieces, said nose pieces each comprising a pad element frame made from a substantially rigid plastic material and a pad element made of a relatively soft resilient plastic material received in the pad element frame thereof, each pad element having a bubble-like convex inner side facing inwardly toward the head of a wearer for resiliently contacting the nose bridge of the wearer each pad element having a perimeter and being solely supported around the perimeter thereof by the respective pad element frame thereof, each pad element also having a concave outer side facing outwardly away from the nose of the wearer and defining an unobstructed hollow open area to permit outward flexing of each pad element in a direction away from the nose of the wearer.

7. In the pair of goggles of claim 6, each of said pad elements being integrally molded in a one piece with the respective pad element frame thereof.

8. In the pair of goggles of claim 6, each of said pad elements including a reinforced outer edge.

9. In the pair of goggles of claim 7, each of said pad element frames being molded with the pad element thereof in an injection molding process.

10. In the pair of goggles of claim 6, said pad elements being of approximately oval configuration.

11. A pair of goggles comprising a frame including a pair of nose pieces and a pair of temples having rear ends extending from said frame, said temples each comprising a pad element adjacent the rear end thereof made from a relatively soft resilient plastic material, said nose pieces also each comprising a pad element made of a relatively soft resilient plastic material, said pad elements of said temples and said nose pieces having bubble-like convex inner sides facing inwardly toward the head and nose bride, respectively, of the wearer, each pad element also having a concave outer side facing outwardly away from the wearer and defining an unobstructed, hollow open area to permit outward flexing of each pad element in a direction away form the wearer.

12. In the pair of goggles of claim 11, each of said temples comprising a basic body portion made from a relatively hard plastic material and one of said pad elements integrally molded in one piece therewith.

13. In the pair of goggles of claim 11, each of said nose pieces comprising a basic body portion made form a relatively hard plastic and one of said pad elements integrally molded in one piece therewith.

14. In the pair of goggles of claim 11, each of said pad elements including a reinforced outer edge.

15. In the pair of goggles of claim 11, each of said pad elements being of approximately oval configuration.

* * * * *